United States Patent
Zhang et al.

(10) Patent No.: US 7,579,599 B2
(45) Date of Patent: Aug. 25, 2009

(54) PARAMETER ADJUSTMENT FOR MEDICAL DEVICE

(75) Inventors: Nan Zhang, Knoxville, TN (US);
Volker Matschl, Knoxville, TN (US);
Niraj K. Doshi, Knoxville, TN (US);
Matthias J. Schmand, Lenoir City, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 101 days.

(21) Appl. No.: 11/941,562

(22) Filed: Nov. 16, 2007

(65) Prior Publication Data

US 2009/0072151 A1 Mar. 19, 2009

Related U.S. Application Data

(60) Provisional application No. 60/973,337, filed on Sep. 18, 2007.

(51) Int. Cl.
*G01T 1/164* (2006.01)

(52) U.S. Cl. .................................. 250/363.03
(58) Field of Classification Search . 250/363.01–363.1, 250/207, 252, 366; 378/111, 98.8
See application file for complete search history.

(56) References Cited

U.S. PATENT DOCUMENTS

| | | | |
|---|---|---|---|
| 3,560,744 A * | 2/1971 | Jordan | 250/252.1 |
| 3,832,542 A * | 8/1974 | Bartlett et al. | 250/363.01 |
| 3,984,689 A * | 10/1976 | Arseneau | 250/369 |
| 5,525,794 A * | 6/1996 | Gibbons | 250/207 |
| 7,247,855 B2 * | 7/2007 | Castellane et al. | 250/363.01 |

OTHER PUBLICATIONS

Liu et al., "A gain-programmable transit-time-stable and temperature-stable PMT voltage divider," 2004, IEEE Transactions on Nuclear Science, vol. 5, pp. 2558-2562.*

Bauer et al., "Dynode-timing method for PET block-detectors," 2006, IEEE Nuclear Science Symposium Conference Record, vol. 5, pp. 3053-3056.*

Liu et al., "A gain-programmable transit-time-stable and temperature-stable PMT voltage divider," 2004, IEEE Transactions on Nuclear Science, vol. 5, pp. 3101-3104.*

* cited by examiner

*Primary Examiner*—David P Porta
*Assistant Examiner*—Kiho Kim

(57) ABSTRACT

A medical device with a high voltage connection line for carrying a high DC supply voltage has a control unit generating said high DC supply voltage which is fed through a first AC block unit to said high voltage connection line and generating a digital control signal fed through a first AC coupling unit to said high voltage connection line, and a remotely located unit a second AC block unit coupled to said high voltage connection line for receiving said high DC supply voltage and a second AC coupling unit coupled to said high voltage connection line for receiving said digital control signal.

25 Claims, 6 Drawing Sheets

PARAMETER ADJUSTMENT FOR MEDICAL DEVICE

RELATED APPLICATIONS

This application claims the benefit of U.S. Provisional Application Ser. No. 60/973,337 filed on Sep. 18, 2007, the entire disclosure of which is incorporated herein by reference.

FIELD

The present invention concerns circuits for adjusting a parameter through a supply line of a medical device.

BACKGROUND

In the field of medical image technology such as Positron Emission Tomography (PET) or gamma cameras, often a remote detector unit separated from a control unit is used. In a PET scanner 100, as for example shown in FIG. 1, a plurality of scintillators 130 and associated photomultiplier tubes (PMT) 110 or avalanche photodiodes (APD) are usually arranged in a circle of a detector ring 130. Such a detector ring 130 surrounds the patient to be scanned. To conduct a so-called PET scan, a short-lived radioactive tracer isotope, which decays by emitting a positron, is injected usually into the blood circulation of a living subject. After the metabolically active molecule becomes concentrated in tissues of interest, the research subject or patient is placed in the imaging scanner. The molecule most commonly used for this purpose is fluorodeoxyglucose (FDG), a sugar, for which the waiting period is typically an hour.

As the radioisotope undergoes positron emission decay, it emits a positron, the antimatter counterpart of an electron. After traveling up to a few millimeters the positron encounters and annihilates with an electron, producing a pair of gamma photons moving in almost opposite directions. These are detected when they reach a scintillator material in the scanning device, creating a burst of light which is detected by photomultiplier tubes (PMT) or silicon avalanche photodiodes (Si APD). The technique depends on simultaneous or coincident detection of the pair of photons.

A PMT or APD can be used in many imaging systems, such as PET scanners and gamma cameras. Each PMT or APD produces one or more signals that need to be processed to generate an image from a plurality of single events that are detected by a PMT. Both, a PMT and an APD require generally a high bias voltage which has to be supplied by a central often remotely located control device. FIGS. 2 and 3 show different embodiments for exemplary conventional PMTs. According to FIG. 2, a positive high bias voltage, for example, between 500 to 3000 V, is supplied to a resistor network 240-249 through terminal 230. Resistor network 240-249 is coupled between the cathode K and anode A of the PMT. The nodes between the resistors 240-249 are coupled with a plurality of dynodes D1-D10. The output signal can be obtained at terminal 220 and is decoupled via a capacitor 210 from the high bias voltage. The resistor network is designed such that a proper voltage gradient is set up between the dynodes D1-D10. This voltage gradient can be adjusted by a potentiometer 260 which is, for example, coupled with dynode D7 as shown in FIG. 2. However, other adjustment methods of the voltage gradient are also possible.

FIG. 3 shows another embodiment using a negative high bias voltage applied between a resistor network 340-348 coupled between the cathode K and the last dynode D10 via terminal 320. Again a potentiometer 360 coupled to an intermediate dynode D7 is used to adjust the voltage gradient. In this embodiment, the output signal can be received directly from the anode A via terminal 310.

FIG. 4 shows a respective high voltage bias circuit 400 as used for an avalanche photo diode detectors. A resistor network 420, 430, 440 is designed to adjust a high voltage received at terminal 410 by means of for example a manual potentiometer 430. The adjusted voltage is fed to the avalanche photo diode 460 through another resistor 450. The output signal is decoupled from diode 460 by means of a capacitor 470 and fed to the input of an operational amplifier 495 comprising a feedback network 480, 490. The output signal is fed to a terminal 405.

In either embodiment, the high bias voltage needs to be provided by a remote control unit. Thus, a respective high voltage line is provided between the control unit and the detector ring 130. In conventional systems the high voltage bias is adjusted by conventional potentiometers as shown in FIGS. 2-4.

Thus, there exists a need for an improved system that allows for a remote control of the voltage gradient or a remote control of the bias of a PMT or APD.

SUMMARY

According to an embodiment, a medical device may comprise a high voltage connection line for carrying a high DC supply voltage; a control unit generating said high DC supply voltage which is fed through a first AC block unit to said high voltage connection line and generating a digital control signal fed through a first AC coupling unit to said high voltage connection line; and a remotely located unit a second AC block unit coupled to said high voltage connection line for receiving said high DC supply voltage and a second AC coupling unit coupled to said high voltage connection line for receiving said digital control signal.

According to a further embodiment, the medical device may further comprise a first digital control unit coupled with a said first AC coupling unit through a first isolator. According to a further embodiment, the medical device may further comprise a second digital control unit coupled with a said second AC coupling unit through a second isolator. According to a further embodiment, the first and/or second AC coupling unit may be a RF transformer or a capacitor. According to a further embodiment, the first isolator may be an optocoupler or a transformer. According to a further embodiment, the first isolator may operating bidirectional. According to a further embodiment, the second isolator can be an opto-coupler or a transformer. According to a further embodiment, the second isolator can be operating bidirectional. According to a further embodiment, the first and/or second AC block unit can be an inductor. According to a further embodiment, the medical device may comprise a detector unit being biased by said high DC supply voltage and may comprise a digitally controlled adjustment unit for adjusting the high DC supply voltage, wherein the digitally controlled adjustment unit can be controlled by the digital control signal. According to a further embodiment, the remotely located unit may comprise a low supply voltage coupled to the high voltage connection line for generating a supply voltage for the digitally controlled adjustment unit. According to a further embodiment, the detector unit can be a photomultiplier tube or an avalanche photo diode. According to a further embodiment, the digitally controlled adjustment unit can be a digital potentiometer. According to a further embodiment, the digitally controlled adjustment unit can be a digital to analog converter or EEPROM.

According to another embodiment, a method of operating a medical device having a control unit generating a high DC supply voltage and a digital control signal, and a remotely located unit receiving said high DC supply voltage through a single high voltage connection line, may comprise the steps of: during a setup or adjustment mode: —feeding said high DC voltage onto said high voltage connection line through a first AC block unit; —feeding said digital control signal onto said high voltage connection line through a first AC coupling unit; —receiving said high DC supply voltage and receiving said digital control signal through a second AC block unit and second AC coupling unit, respectively; —adjusting said high DC supply voltage according to said digital control signal in said remotely located unit; and during normal operation mode: —feeding said high DC voltage onto said high voltage connection line through a first AC block unit and receiving said high DC voltage through a second AC block unit while no digital control signal is present on said high voltage connection line.

According to a further embodiment, the remotely located unit can be a detector unit comprising a plurality of photomultiplier tubes or avalanche photo diodes. According to a further embodiment, the digital control signal may adjust a voltage gradient applied to the photomultiplier tubes or avalanche photo diodes. According to a further embodiment, the step of adjusting can be performed with at least one digitally controlled potentiometer, digital-to-analog converter, or EEPROM. According to a further embodiment, the digital control signal can be fed onto said high voltage connection line via an opto-coupler or RF transformer.

According to another embodiment, a positron emitter tomography (PET) scanner may comprise a high voltage connection line for carrying a high DC supply voltage; a control unit generating said high DC supply voltage which is fed through a first AC block unit to said high voltage connection line and generating a digital control signal fed through a first AC coupling unit to said high voltage connection line; and a remotely located detector unit comprising a second AC block unit coupled to said high voltage connection line for receiving said high DC supply voltage and a second AC coupling unit coupled to said high voltage connection line for receiving said digital control signal, said detector unit being biased by said high DC supply voltage and comprising a digitally controlled adjustment unit for adjusting said high DC supply voltage, wherein said digitally controlled adjustment unit is controlled by said digital control signal.

According to a further embodiment, the PET scanner may further comprise a first digital control unit coupled with a first AC coupling unit through a first isolator and a second digital control unit coupled with a second AC coupling unit through a second isolator. According to a further embodiment, the first and/or second AC coupling unit can be a RF transformer or a capacitor, the first isolator can be an opto-coupler or transformer, the second isolator can be an opto-coupler or a transformer, and the first and/or second AC block unit can be an inductor. According to a further embodiment, the detector unit may comprise a plurality of photomultiplier tubes or avalanche photo diodes. According to a further embodiment, the digitally controlled adjustment unit can be a digital potentiometer, a digital to analog converter or EEPROM.

BRIEF DESCRIPTION OF THE DRAWINGS

A more complete understanding of the present disclosure thereof may be acquired by referring to the following description taken in conjunction with the accompanying drawings wherein.

Figure 1:
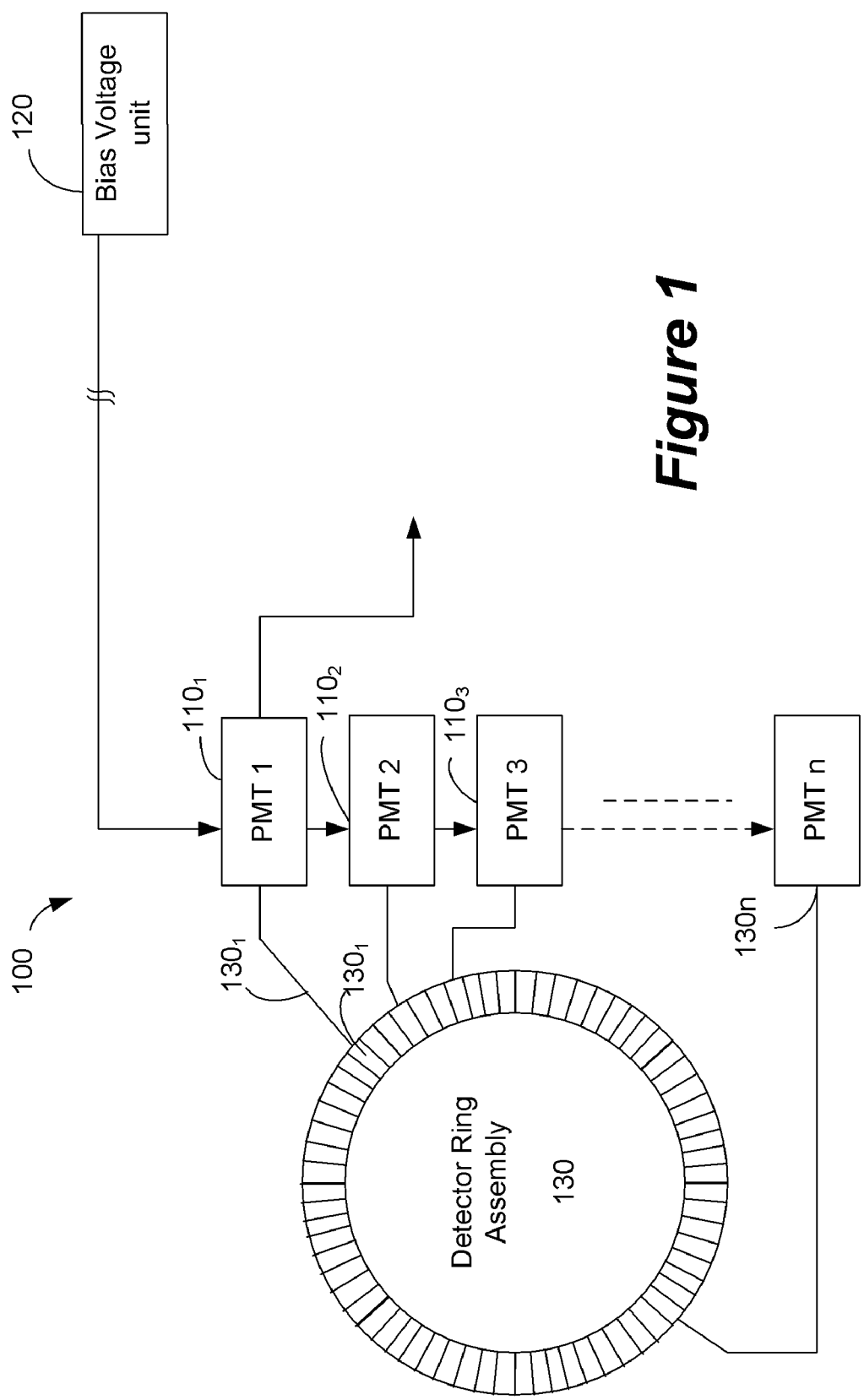
FIG. 1 shows a simplified block diagram of an embodiment of parts of a PET scanner.

While the present disclosure is susceptible to various modifications and alternative forms, specific exemplary embodiments thereof have been shown in the drawings and are herein described in detail. It should be understood, however, that the description herein of specific exemplary embodiments is not intended to limit the disclosure to the particular forms disclosed herein, but on the contrary, this disclosure is to cover all modifications and equivalents as defined by the appended claims.

DETAILED DESCRIPTION

PET scanners using PMTs or APDs as detectors can be operated in different modes. For example, during a set-up mode which can be used, for example, to configure or adjust the voltage gradient or high voltage bias, the control device may communicate bidirectionally or unidirectionally with the remote detector device to perform the respective configuration or adjustment. However, during the actual run mode in which an object/patient is actually scanned, most of the communication runs from the detector to the remote control device transmitting a plurality of data that is to be processed by the remote control device. Hence, there will be generally no digital communication from the remote control device to the detector device for the purpose of adjusting the high voltage during a patient scan.

Therefore, according to an embodiment, the high voltage supply line can be used to also carry data information as no such information will be transmitted during an actual scan. The high voltage used for biasing the PMTs or APDs needs to be noise free to avoid contamination of the imaging signals. In other words, even though the mixed digital signals in the high voltage line, according to an embodiment, could increase noise which potentially decreases the detector performance during a high voltage setup or adjustment routine, these digital noises would not be present during the data acquisition phase. Moreover, the setup or adjustment routine of the high voltage can be performed sequentially, meaning in a first step the data is transmitted to set up or adjust the voltage gradient, for example using a digital potentiometer or an analog to digital converter and a following measurement is performed while no data is transmitted. Thus, no noise would be introduced during the actual scan. However, by using the high voltage supply line for transmitting data for purposes of set up, calibration, or adjustment, no additional wiring between a remote control device and the actual detector device would be necessary. In addition, existing systems that do not provide for such a remote control functionality can be upgraded without requiring to run additional wiring between the remote control device and the detector device. This can result in significant cost savings.

Figure 2:
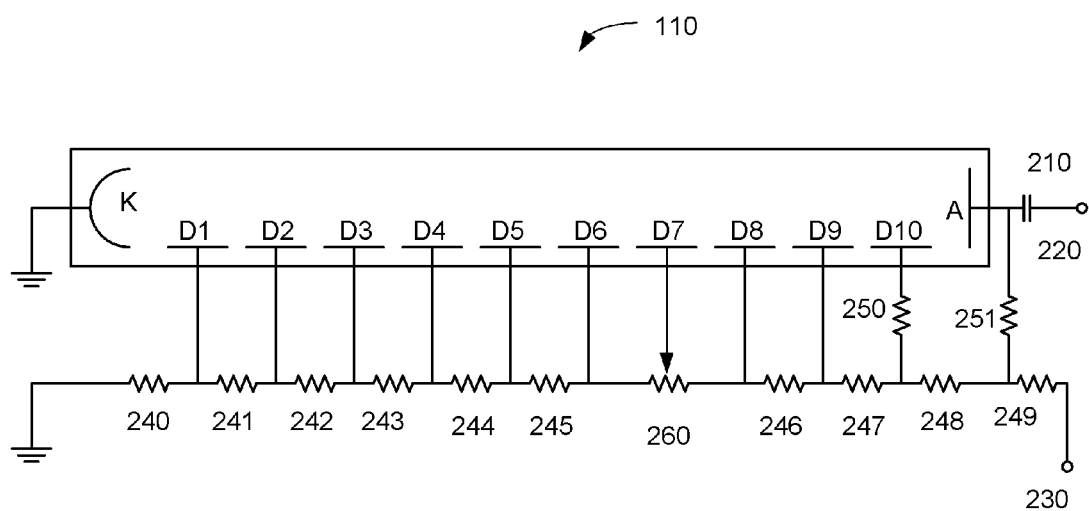
FIGS. 2 and 3 show different conventional bias circuits for PMTs.
Figure 3:
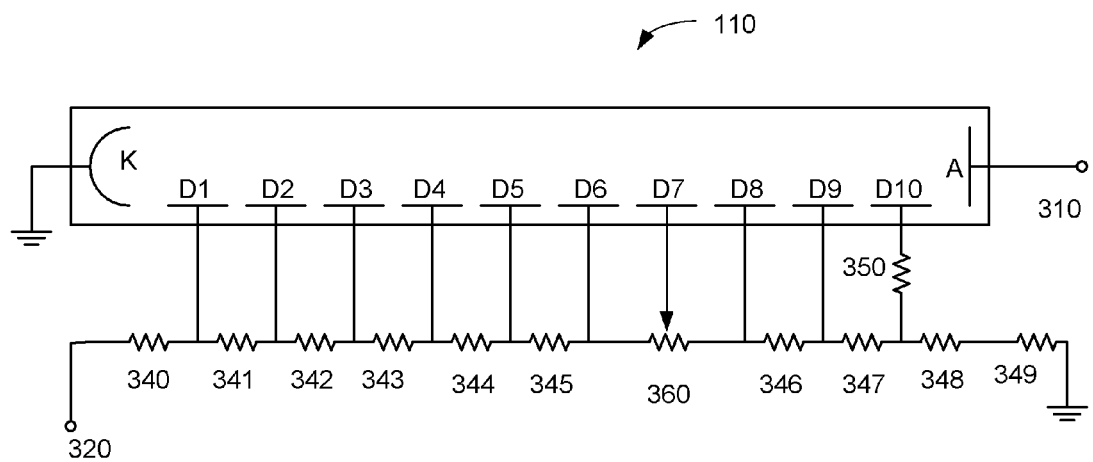
Figure 4:
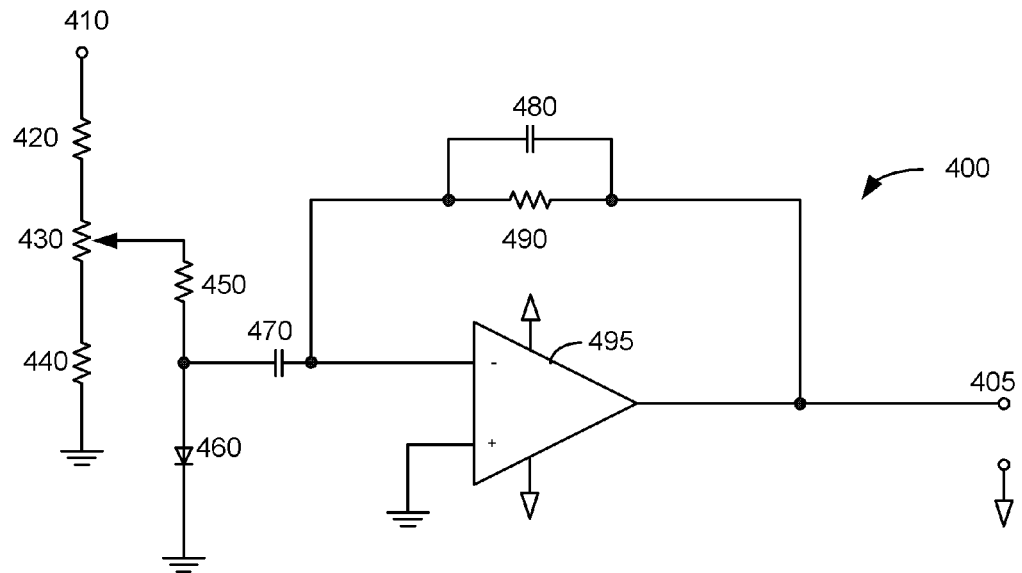
FIG. 4 shows another conventional bias circuits for an APD.
Figure 5:
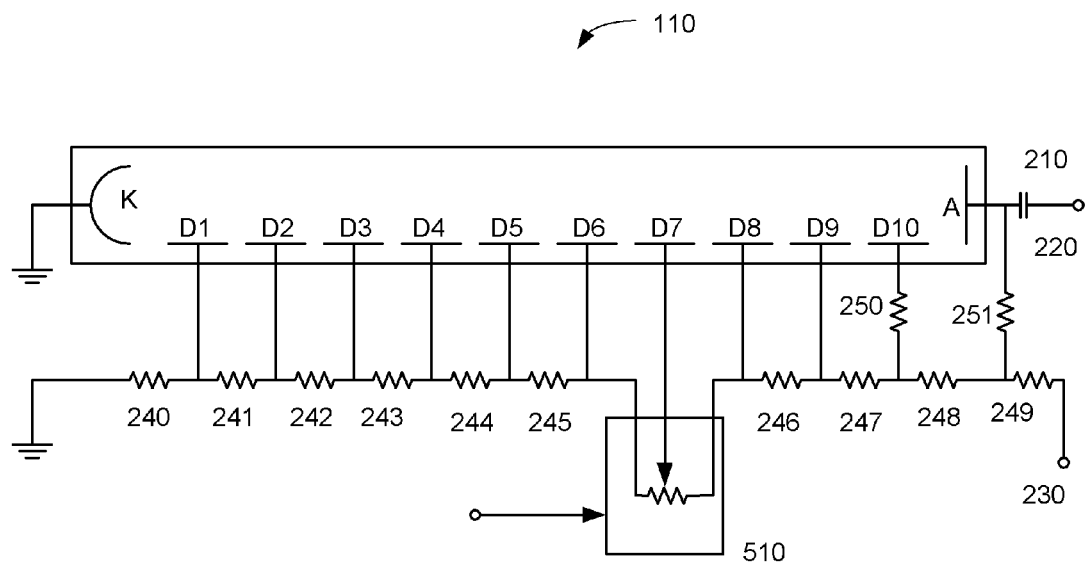
FIG. 5 shows a first embodiment of a remotely controllable PMT.
Figure 6:
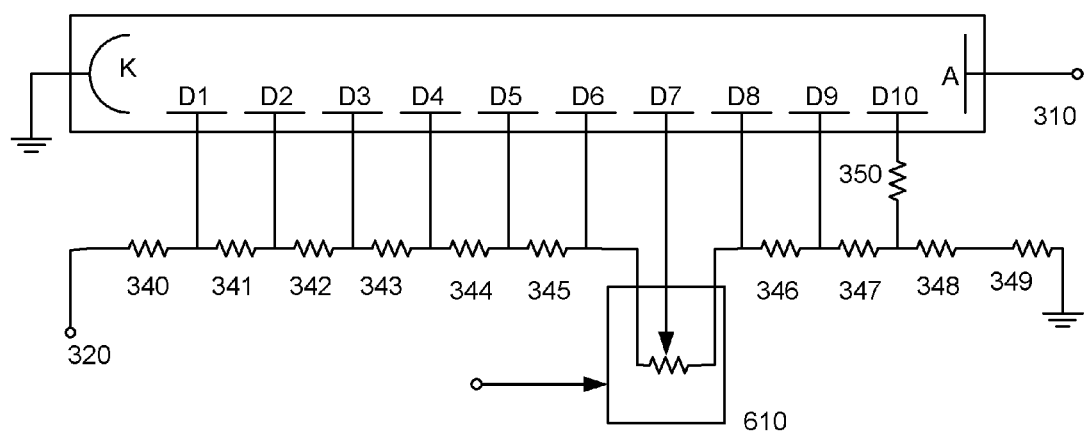
FIG. 6 shows a second embodiment of a remotely controllable PMT.

FIGS. 5 and 6 show different embodiments of bias circuits usable for a PMT for which the voltage gradient can be remotely controlled. To this end, manual potentiometers 260; 360 of the respective circuits of FIGS. 2 and 3 are replaced by digitally controlled potentiometers 510; 610, respectively. Each digital potentiometer comprises a control input 520; 620 that may have a digital interface including for example, a chip select input and a serial or parallel data input.

Figure 7:
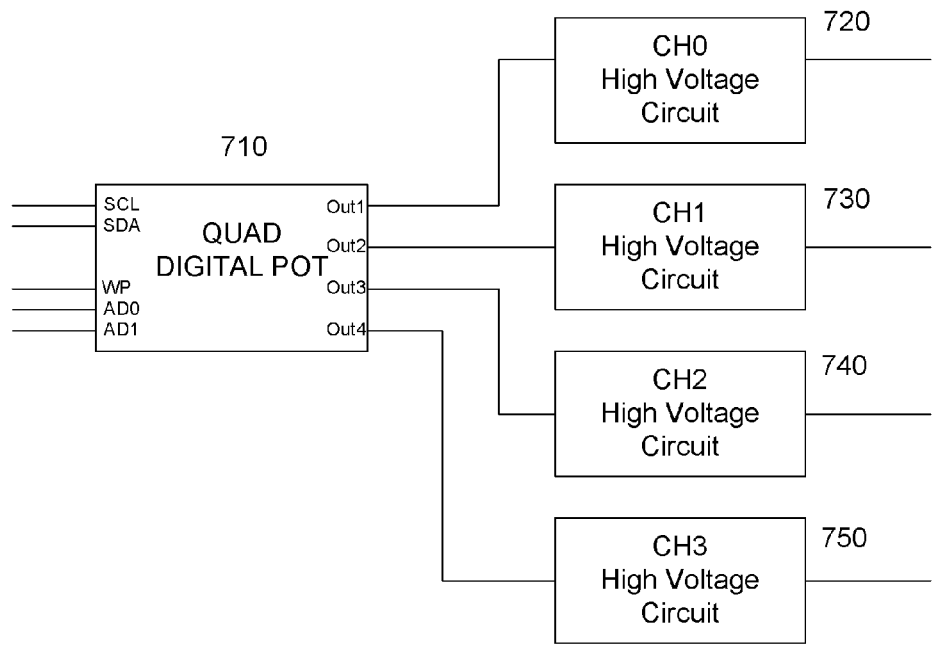
FIG. 7 shows another embodiment for remotely controllable bias voltages.

According to yet another embodiment, as for example shown in FIG. 7, an integrated circuit device 710 may provide for multiple digital potentiometers. As depicted in FIG. 7, a digital quad potentiometer can be used to provide for four independent analog output signals. The digital quad potentiometer 710 can be programmed via a standard serial interface such as a serial peripheral interface (SPI), I²C, or any other suitable interface. It may have a write protection input and address inputs to select one of the four potentiometers. The four output signals may be fed to respective high voltage circuits 720, 730, 740, and 750 that convert the resistor value into a high voltage signal that can be fed to the respective PMT or APD. According to one embodiment a single or a plurality of high voltage signals can be provided for each PMT or APD to allow for a flexible voltage gradient adjustment. The same digitally controlled adjustment principles can be used for circuits using APDs.

Figure 8:
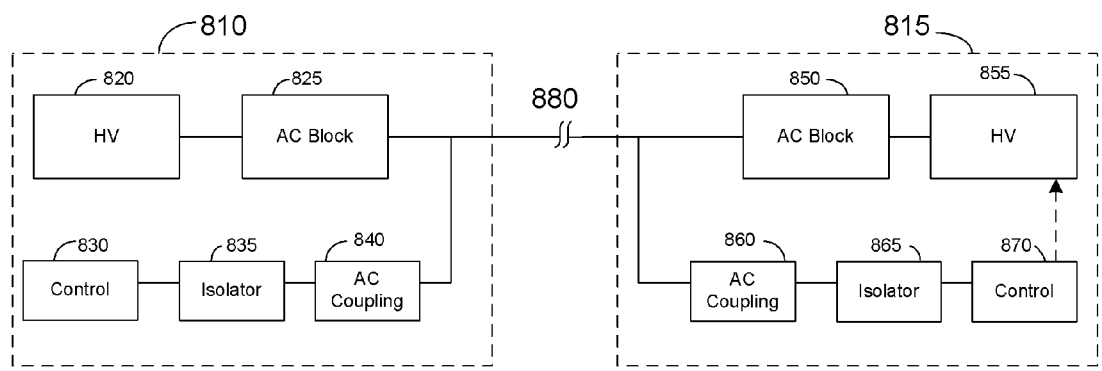
FIG. 8 shows an embodiment of a control circuit and a remote PMT or APD device.

FIG. 8 shows the actual coupling between a control device 810 and a remotely arranged detector ring assembly 820 that are coupled via a high voltage bias line 880. A high voltage bias generator 820 in the control device 810 is coupled to the high voltage bias line 880 via an AC block unit 825. The digital control signals are generated in control unit 830 and sent via an optional isolator 835 to an AC coupling unit 840 that feeds the digital control signals onto the high voltage bias line 880. The detector ring assembly or any other remote device has a similar structure with an AC block unit 850 that separates AC signals from the high bias voltage fed to the detector unit 855. Also, an AC coupling unit 860 is coupled with the high voltage bias line 880 to forward the data signals via an optional isolator unit 865 to the digital control receiver 870. The receiver 870 sends the respective digital control signals to the detector unit 855. As shown in FIG. 8, the arrangement is symmetrical and, thus, allows communication in both directions depending on the application. For example, according to an embodiment, unit 870 can be a digital control transceiver and provide for feed back signals to the control device 810.

Figure 9:
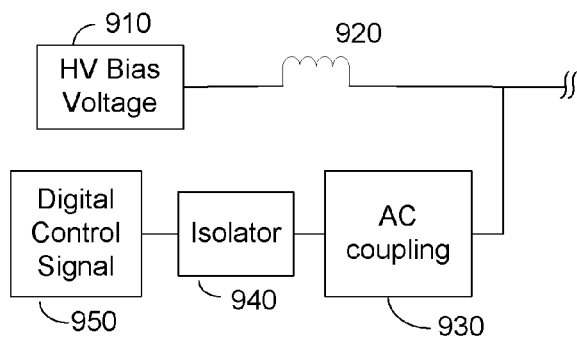
FIG. 9 shows an embodiment of a PMT or APD coupled through a single supply line.

FIG. 9 shows an embodiment of a device coupled to a high voltage line for receiving and/or transmitting digital data in more detail. A high voltage unit for receiving or providing a high voltage is generally denoted as unit 910. The AC block unit may be formed by an inductor 920. AC coupling unit 930 may, for example, include a capacitor or a transformer to separate the high DC voltage of line 880 from the following circuits. Furthermore, optionally an isolator can be provided which again may be a transformer or an opto-coupler that further isolates the following digital controller 950 from the high voltage line 880.

Figure 10:
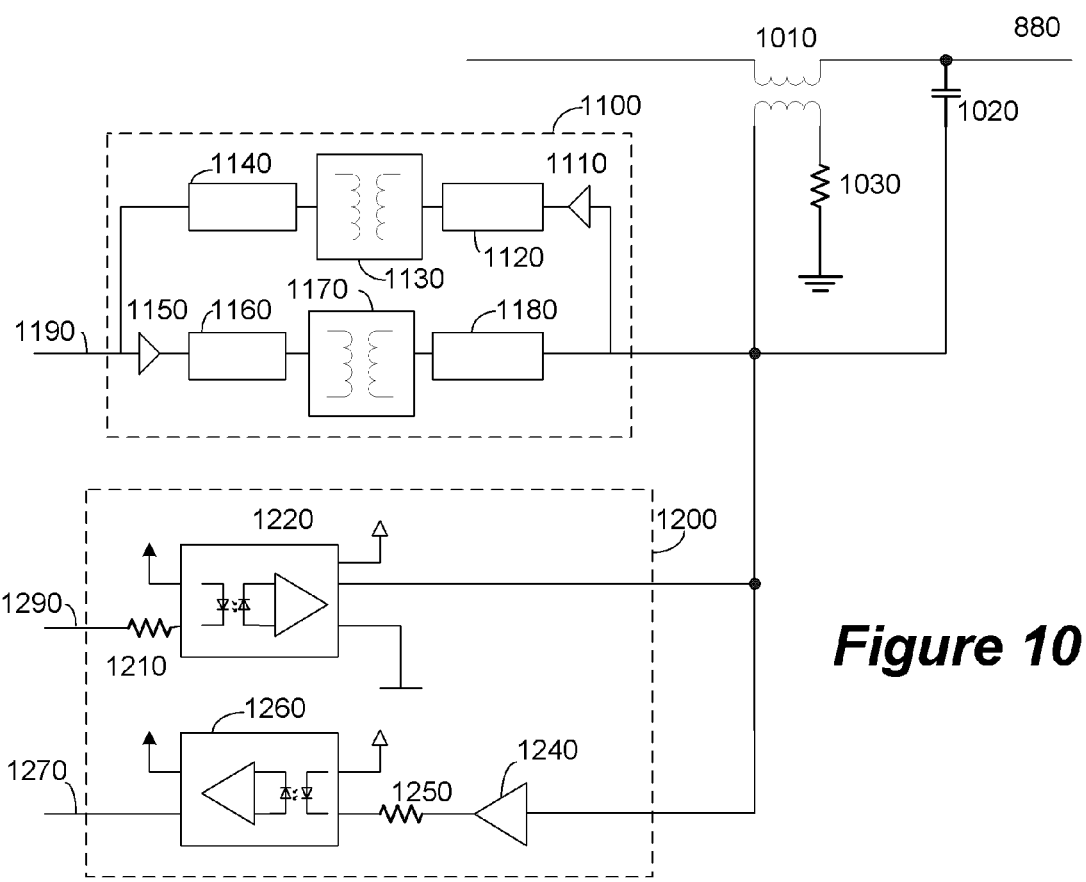
FIG. 10 shows different embodiment of a PMT or APD coupled through a single supply line.

FIG. 10 shows details of different coupling and isolator units. A first embodiment of an AC coupling unit 930 is shown with a transformer 1010 comprising a first winding which is serially coupled into high voltage line 880. A second winding is, for example, coupled with an isolator unit and via a resistor 1030 with ground. Alternatively, FIG. 10 also shows a capacitor 1020 coupled between the high voltage line 880 and an isolator unit. FIG. 10 shows also two different embodiments for isolator unit 940. A first embodiment 1100 comprises transformers 1130 and 1170. the receiving path comprises a driver 1110 followed by an encoder 1120, transformer 1130, and decoder 1140 coupled to a single wire 1190 for forming an I²C or SPI interface. The transmitting path comprises driver 1150 connected to the single wire 1190 followed by encoder 1160, transformer 1170, and decoder 1180.

Another bidirectional interface is shown with unit 1200 that uses opto-couplers. This embodiment provides for separate input and output lines 1270 and 1290. Input line 1290 is coupled with the input side of opto-coupler 1220 via resistor 1210. The output side of opto-coupler 1220 is coupled with the AC coupling unit. Output line 1270 is coupled with the output side of second opto-coupler 1260 whose input side is coupled to the output of driver 1240 via resistor 1250. The input of driver 1240 is coupled with the AC coupling unit.

The arrangement may be operated as follows. During a setup mode such as for configuring or adjusting of the high bias voltage, there is usually no or little data transmission from the PMTs or APDs to the remote controller. Thus, any modulation of the DC high bias voltage will have no influence on a scan results. Hence, there is no need to have extra immunization efforts such as power supply regulation and rejection to reduce any noise. A simple inductor will, therefore suffice to decouple the AC data signals from the DC high voltage. During the setup mode, digital control signal are sent through the high voltage bias line to adjust, for example, the gain of the PMT anode output A or the output of an APD. The digitally controlled potentiometers receive the transmitted digital control signals and can, thus, be adjusted accordingly. According to other embodiments instead of digital control potentiometers, a digital controlled EEPROM, digital-to-analog converters or other suitable circuitry can be used to adjust a parameter in the remote medical device.

Different digital interfaces can be used as shown in FIGS. 7-10. As stated above, for example, an I²C, SPI or 1-wire protocol can be used. These signals can then be used for detector high voltage setup and gain adjustment within the control and detector units. As stated above, for de-coupling of the high DC bias voltage and the AC signals carrying the digital control signals a simple inductor may be used. This sufficiently blocks the AC signals from the DC high voltage generator or receiver. Even though such a simple AC block would not completely eliminate the digital AC signal from coupling to the internal HV line, this will not cause any problems because the AC digital signal is quiet during data acquisition operations.

According to various embodiments, a surface-mount high voltage capacitor or miniature RF transformer (XFMR) may be chosen for the AC coupling function to couple the digital signals and isolate the high voltage to subsequent digital circuits as shown in FIGS. 9 and 10. In embodiments of PET detectors that are embedded or integrated in MRI devices a capacitor is of course the preferred coupling device.

The high voltage line 880 usually references to analog ground (AGND). however, the digital control signal could come from a dedicated I²C, SPI or 1-wire controller, as well as from a micro-control-unit (MCU) or a field programmable gate array (FPGA). Generally, all these digital circuits would refer to a digital ground (DGND). As stated above, to isolate AGND from DGND, more importantly, to isolate noise from DGND coupling to AGND, a low cost isolator can be optionally inserted between the digital control circuit and the AC coupling capacitor or XFMR. As shown in FIGS. 9 and 10, a conventional opto-coupler which is an integrated circuit combining a light source and a photosensitive detector, or a transformer based device such as an iCoupler® can be used.

Figure 11:
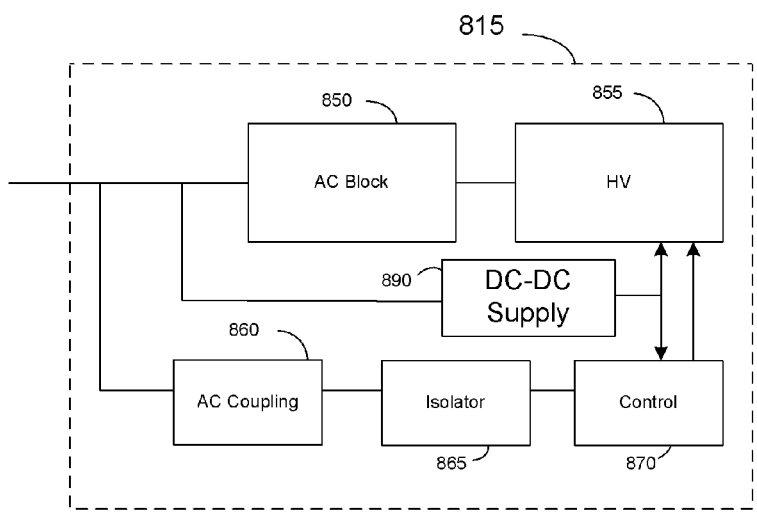
FIG. 11 shows another embodiment of a remote PMT or APD device.

Since the digital circuits in the detector requires low voltage DC power, for example a 3.3 V DC supply, a DC-DC circuit 890 as shown in FIG. 11 can be built to transfer electric power from the HV line to supply the digital circuitry 870 and if necessary to any voltage gradient adjustment circuit in the detector unit 855. In this case, the high voltage and supply current are converted to the low voltage and current for digital circuits. With such an embodiment, high power efficiency in the circuits is maintained and the current load from the high voltage power supply is minimized. DC-DC converters 890 can also easily handle the polarity issues between the potential negative high voltage and the positive low voltage DC power.

While embodiments of this disclosure have been depicted, described, and are defined by reference to example embodiments of the disclosure, such references do not imply a limitation on the disclosure, and no such limitation is to be inferred. The present invention is in particular not restricted to PET scanners but can be applied to any other medical device that uses bias voltage supply lines. The subject matter disclosed is capable of considerable modification, alteration, and equivalents in form and function, as will occur to those ordinarily skilled in the pertinent art and having the benefit of this disclosure. The depicted and described embodiments of this disclosure are examples only, and are not exhaustive of the scope of the disclosure.

What is claimed is:

1. A medical device comprising:
   a high voltage connection line for carrying a high DC supply voltage;
   a control unit generating said high DC supply voltage which is fed through a first AC block unit to said high voltage connection line and generating a digital control signal fed through a first AC coupling unit to said high voltage connection line; and
   a remotely located unit comprising or the like a second AC block unit coupled to said high voltage connection line for receiving said high DC supply voltage and a second AC coupling unit coupled to said high voltage connection line for receiving said digital control signal.

2. The medical device according to claim 1, further comprising a first digital control unit coupled with a said first AC coupling unit through a first isolator.

3. The medical device according to claim 2, further comprising a second digital control unit coupled with a said second AC coupling unit through a second isolator.

4. The medical device according to claim 3, wherein said second isolator is an opto-coupler or a transformer.

5. The medical device according to claim 2, wherein said first isolator is an opto-coupler.

6. The medical device according to claim 2, wherein said first isolator is a transformer.

7. The medical device according to claim 2, wherein said first isolator is operating bidirectional.

8. The medical device according to claim 2, wherein said second isolator is operating bidirectional.

9. The medical device according to claim 1, wherein said first and/or second AC coupling unit is a RF transformer or a capacitor.

10. The medical device according to claim 1, wherein said first and/or second AC block unit is an inductor.

11. The medical device according to claim 1, further comprising a detector unit being biased by said high DC supply voltage and comprising a digitally controlled adjustment unit for adjusting said high DC supply voltage, wherein said digitally controlled adjustment unit is controlled by said digital control signal.

12. The medical device according to claim 11, wherein the remotely located unit comprises a low supply voltage coupled to said high voltage connection line for generating a supply voltage for said digitally controlled adjustment unit.

13. The medical device according to claim 12, wherein said digitally controlled adjustment unit is a digital potentiometer.

14. The medical device according to claim 12, wherein said digitally controlled adjustment unit is a digital to analog converter or EEPROM.

15. The medical device according to claim 11, wherein said detector unit is a photomultiplier tube or an avalanche photo diode.

16. A method of operating a medical device having a control unit generating a high DC supply voltage and a digital control signal, and a remotely located unit receiving said high DC supply voltage through a single high voltage connection line, the method comprising the steps of:
   during a setup or adjustment mode:
      feeding said high DC voltage onto said high voltage connection line through a first AC block unit;
      feeding said digital control signal onto said high voltage connection line through a first AC coupling unit;
      receiving said high DC supply voltage and receiving said digital control signal through a second AC block unit and second AC coupling unit, respectively;
      adjusting said high DC supply voltage according to said digital control signal in said remotely located unit;
   during normal operation mode:
      feeding said high DC voltage onto said high voltage connection line through a first AC block unit and receiving said high DC voltage through a second AC block unit while no digital control signal is present on said high voltage connection line.

17. The method according to claim 16, wherein the remotely located unit is a detector unit comprising a plurality of photomultiplier tubes or avalanche photo diodes.

18. The method according to claim 17, wherein the digital control signal adjusts a voltage gradient applied to said photomultiplier tubes or avalanche photo diodes.

19. The method according to claim 16, wherein said step of adjusting is performed with at least one digitally controlled potentiometer, digital-to-analog converter, or EEPROM.

20. The method according to claim 16, wherein the digital control signal is fed onto said high voltage connection line via an opto-coupler or RF transformer.

21. A positron emitter tomography (PET) scanner comprising:
   a high voltage connection line for carrying a high DC supply voltage;
   a control unit generating said high DC supply voltage which is fed through a first AC block unit to said high voltage connection line and generating a digital control signal fed through a first AC coupling unit to said high voltage connection line;
   a remotely located detector unit comprising a second AC block unit coupled to said high voltage connection line for receiving said high DC supply voltage and a second AC coupling unit coupled to said high voltage connection line for receiving said digital control signal, said detector unit being biased by said high DC supply voltage and comprising a digitally controlled adjustment unit for adjusting said high DC supply voltage, wherein said digitally controlled adjustment unit is controlled by said digital control signal.

22. The PET scanner according to claim 21, further comprising a first digital control unit coupled with a said first AC coupling unit through a first isolator and a second digital control unit coupled with a said second AC coupling unit through a second isolator.

23. The PET scanner according to claim 21, wherein said first and/or second AC coupling unit is a RF transformer or a capacitor, said first isolator is an opto-coupler or transformer, said second isolator is an opto-coupler or a transformer, and said first and/or second AC block unit is an inductor.

24. The PET scanner according to claim 21, wherein said detector unit comprises a plurality of photomultiplier tubes or avalanche photo diodes.

25. The PET scanner according to claim 21, wherein said digitally controlled adjustment unit is a digital potentiometer, a digital to analog converter or EEPROM.

* * * * *